US010052217B2

(12) United States Patent
Pallari

(10) Patent No.: US 10,052,217 B2
(45) Date of Patent: Aug. 21, 2018

(54) ORTHOTIC OR PROSTHETIC CUSHIONED DEVICE AND METHOD OF MAKING THE SAME

(75) Inventor: Jari Heikki Petteri Pallari, Leuven (BE)

(73) Assignee: Materialise N.V., Leuven (BE)

(*) Notice: Subject to any disclaimer, the term of this patent is extended or adjusted under 35 U.S.C. 154(b) by 925 days.

(21) Appl. No.: 12/636,219

(22) Filed: Dec. 11, 2009

(65) Prior Publication Data

US 2010/0161076 A1 Jun. 24, 2010

(30) Foreign Application Priority Data

Dec. 11, 2008 (GB) .................................. 0822590.6

(51) Int. Cl.
*A61F 5/01* (2006.01)
*A61F 2/78* (2006.01)
(Continued)

(52) U.S. Cl.
CPC ........ *A61F 2/7812* (2013.01); *A41D 13/0156* (2013.01); *A42B 3/124* (2013.01); *A43B 13/182* (2013.01); *A43B 13/183* (2013.01); *A61F 2/5046* (2013.01); *A61F 2002/503* (2013.01); *A61F 2002/505* (2013.01); *A61F 2002/5049* (2013.01); *A61F 2002/5056* (2013.01); *A61F 2002/5073* (2013.01); *A61F 2002/5075* (2013.01); *A61F 2002/5076* (2013.01); *A61F 2002/5079* (2013.01); *A61F 2002/785* (2013.01); *A61F 2005/0197* (2013.01)

(58) Field of Classification Search
CPC ...... A61F 2002/5073; A61F 2002/5075; A61F 2002/5076; A61F 2005/0197; A41D 13/0156; A42B 3/124; A43B 13/182

USPC ....................................................... 623/33, 36
See application file for complete search history.

(56) References Cited

U.S. PATENT DOCUMENTS 2,500,622 A * 3/1950 Aho ................................ 623/36
3,877,076 A * 4/1975 Summers et al. ................ 2/414
(Continued)

FOREIGN PATENT DOCUMENTS

DE 78 10 225 U1 * 7/1978 ............. A42B 3/124
EP 1 369 149 A1 * 12/2003 ......... A41D 13/0156
(Continued)

OTHER PUBLICATIONS

Faustini, et al., "Manufacture of passive dynamic ankle-foot orthoses using selective laser sintering" *IEEE Transactions on Biomedical Engineering* (2008) 55(2): 784-790, Feb. 2008.
(Continued)

*Primary Examiner* — David H Willse
(74) *Attorney, Agent, or Firm* — Patterson & Sheridan LLP

(57) ABSTRACT

Orthotic and prosthetic devices having integrated features such as cushioning features are described, as well as methods for computer aided designing and making of these devices. The orthotic or prosthetic devices comprise a cushioning layer superimposed onto an orthotic or prosthetic shell, the cushioning layer comprising an array (35) of discrete solid and resilient cushioning elements (31). In one preferred embodiment, the cushioning structure is a beam, defined around a centerline of any arbitrary shape. In another preferred embodiment, the cushioning structure has the shape of a spiral.

20 Claims, 9 Drawing Sheets

(51) Int. Cl.
  *A41D 13/015* (2006.01)
  *A43B 13/18* (2006.01)
  *A42B 3/12* (2006.01)
  *A61F 2/50* (2006.01)

(56) References Cited

U.S. PATENT DOCUMENTS

| | | | |
|---|---|---|---|
| 5,141,680 | A | 8/1992 | Almquist et al. |
| 5,192,539 | A | 3/1993 | Van Der et al. |
| 5,343,637 | A * | 9/1994 | Schindler ............. A43B 13/182 36/27 |
| 6,077,300 | A * | 6/2000 | Sabolich et al. ................. 623/37 |
| 6,123,716 | A * | 9/2000 | Augustine et al. ........... 607/104 |
| 6,968,246 | B2 | 11/2005 | Watson et al. |
| 2003/0200677 | A1 * | 10/2003 | Abraham ......................... 36/27 |
| 2004/0143345 | A1 * | 7/2004 | Caspers ........................... 623/36 |
| 2008/0301975 | A1 * | 12/2008 | Fusco ............................... 36/43 |
| 2010/0070051 | A1 * | 3/2010 | Carstens ......................... 623/34 |

FOREIGN PATENT DOCUMENTS

| | | | |
|---|---|---|---|
| WO | WO 97/03626 | 6/1997 | |
| WO | WO 2007/060500 A2 * | 5/2007 | ............... A43B 7/14 |
| WO | WO 2008/061500 A2 * | 5/2008 | ............... A61F 2/80 |

OTHER PUBLICATIONS

Rogers, et al., "Case Report: Variably Compliant Transtibial Prosthetic Socket Fabricated Using Solid Freeform Fabrication" *J. Prosthetics and Orthothotics* (2008) 20: 1-7. Obtained online at http://www.oandp.org/jpo/library/printArticle.asp?printArticleId=2008_01_001 on Oct. 29, 2012.

Gupta, et al., "Design and freeform fabrication of compliant cellular materials with graded stiffness" *Solid Freeform Fabrication Symposium* (D. L. Bourell, J. J. Beaman, R. H. Crawford, H. L. Marcus, C. C. Seepersad and K. L. Wood, Eds.), Austin, TX. (2006) Obtained online at http://www.me.utexas.edu/~ppmdlab/files/SFF.gaurav.FINAL.pdf on Oct. 29, 2012, 17 pages.

* cited by examiner

ORTHOTIC OR PROSTHETIC CUSHIONED DEVICE AND METHOD OF MAKING THE SAME

CROSS-REFERENCE TO RELATED APPLICATIONS

This application claims priority from British Patent Application No. GB 0822590.6, filed Dec. 11, 2008, which is hereby incorporated by reference.

FIELD OF THE INVENTION

The present invention relates generally to the field of orthotic and prosthetic devices and, more specifically, to orthotic and prosthetic devices having cushioning structures as well as methods for computer aided designing and making of these devices.

BACKGROUND TO THE INVENTION

An orthosis is an external insert, device, support or brace designed to support a patient in carrying the loads applied onto them by walking, running, manipulating objects and/or similar activities and/or by repositioning a limb or forcing them to move a certain way. They can also spread the pressure between the body and the shoe/ground/prosthetic over a larger surface area and provide cushioning to the loaded areas.

A prosthetic device is an artificial extension of the human body or a replacement of a lost body part, e.g. to replace a lost limb or any other body part. A prosthetic limb—upper or lower extremity—usually consists of a prosthetic socket which conforms to the residual limb, the artificial limb, such as a hand or leg and some means of attaching the limb to the socket.

Currently the design and manufacture of customized orthoses and prosthetic sockets is a multi-stage and labour intensive process with significant elements of clinical judgement, manufacturing craftsmanship and trial-and-error experimentation. Only a few standardized procedures exist in their design and manufacturing. This can lead to variation in the final product. The lengthy manufacturing process can also delay treatment.

Traditionally the orthoses and prosthetic manufacturing processes are very similar. Initially, a plaster cast of the relevant parts of the limb or residual limb is taken; this is then worked into a positive of the limb/residual limb, where certain interventions are applied by the craftsman manually. The modified positive is then vacuum formed or laminated using thermo-formable plastic. This device is then further modified, finished and fitted to the patient. Further manual modifications may be necessary, especially with prosthetic sockets, or when adding hinges to orthoses. Adding cushioning materials is also one step in the finishing procedure.

This process is completely manual, requiring considerable experience and skill. Each device is also unique, as the work stages are done slightly differently each time. Also, if several persons are working on the same device, each person has a different idea what is required.

In U.S. Pat. No. 6,968,246, a computer assisted system is described to address these issues. In the computer assisted approach, the technician manufacturing the orthoses or prosthesis can input the shape of the limb/residual limb in question into a computer system with the aid of a mechanical or a magnetic digitizer or a 3D laser scanner. This shape is then used to design an orthoses or prosthesis in specialist computer software that decreases the overall volume of the device by certain amounts. A pattern matching this shape can then be manufactured by using a 3D carver and vacuum molded or laminated as in the traditional process.

It is also known from the prior art, as described in the article in Volume 55(2) (2008) of the IEEE Transactions on Biomedical Engineering to Faustini entitled "Manufacture of passive dynamic ankle-foot orthoses using selective laser sintering.", that customized orthotic or prosthetic devices may be manufactured using Selective Laser Sintering (SLS), a Rapid Prototyping and Manufacturing (RP&M) technique, where RP&M can be defined as a group of techniques used to quickly fabricate a scale model of an object typically using 3-D computer aided design (CAD) data of the object.

Cushioning is applied to these devices by using different materials attached on the main body of the device. The properties of the cushioning (e.g. varying from soft to hard) can be adjusted only by changing the material or the thickness of the cushioning element, which usually changes the shape of the surface. The cushioning material and thickness is typically homogeneous over the pressure carrying area. Local modifications, like local cushions such as metatarsal pads or bars, cutouts for the plantar fascia, etc. can be made manually by cutting out material or adding more of the same or a different material on top of the existing one to treat certain conditions. The purpose of cushioning is to absorb the forces placed on it through compression or elastic or plastic deformation of the cushioning material so that the user of the device with the cushioning will not have to absorb as much of the forces.

However, the need for time-consuming manual tasks makes the overall process slow and specialist equipment and supplies are needed. If the design is incorrect, the whole process has to be restarted. Moreover, the manual process of locating added cushioning features may result in problems with quality and consistency as every craftsman works slightly differently and creates different orthoses. The computer assisted process may alleviate some of these issues related in creating the positive and making the interventions to it, but adds more process steps in the orthoses creation chain and adds extra investment in training, equipment, milling materials which also create a lot of waste—without solving the problems with traditional manufacturing completely. The lamination/vacuum forming will still have to be done manually, as will the addition of features such as cushioning, hinges, cutouts, etc.

Patent application WO 97/03626 describes a modular interface connector for a prosthetic limb. The modular interface connector includes an interface cushion having a feathered periphery of tapered blades, which conforms to the inner surface of the socket of the residual limb.

The paper by Bill Rogers and others, "Case Report: Variably Compliant Transtibial Prosthetic Socket Fabricated Using Solid Freeform Fabrication", Journal of Prosthetics and Orthothotics, 2008; 20:1-7, describes sockets fabricated using selective laser sintering, wherein compliance is provided by a diaphragm spring that is integrated into the socket wall.

In the article "Design and freeform fabrication of compliant cellular materials with graded stiffness" from the Solid Freeform Fabrication Symposium (Gupta, G., et al.), layer manufactured cushioning structures for prosthetic applications are described as solid base material arranged in cellular topologies that permit high levels of elastic deformation. The structures presented in this article may solve some of the problems found in prior art, but they do not offer all the advantages of the present invention.

SUMMARY OF THE INVENTION

Accordingly, those skilled in the art of orthotic and prosthetic device manufacturing and the like recognize the need for integrated features such as cushioning features as well as suitable manufacturing methods for orthoses and prosthesis enabling at least some of the advantages of the prior art procedures, yet having less limitations associated therewith. The cushioning properties of a cushioning structure refer to it being compressibly resilient. This can mean the compressibility of the material, the elastic deformation of the structure or a combination thereof. This can be measured for example with the standard ISO 7619 or ASTM D2240. The areas of the orthotic/prosthetic device that are cushioned using the embodiments described in this invention have the Shore value of 20-90 when measured using an OO durometer using these standards. This cushioning structure is not foam. Each shape and feature in the cushioning structure is determined deliberately either by the user or the computer system. Shapes and features in the cushioning structure can be seamlessly adjusted as needed by the computer system or the user.

The present invention provides orthotic and prosthetic devices having integrated features such as cushioning features, as well as methods for computer aided designing and making of these devices. In the most preferred embodiment, the orthotic or prosthetic devices comprise a cushioning layer superimposed onto an orthotic or prosthetic shell, the cushioning layer comprising an array of discrete solid and resilient cushioning elements that are formed in an integral manner with the shell. In one embodiment of the invention, the cushioning elements and the shell are formed from the same material. In one preferred embodiment, said cushioning structure comprises a cushioning element that is a beam, defined around a centerline of any arbitrary shape. In another preferred embodiment, said cushioning structure comprises a cushioning element that has the shape of a spiral.

In preferred embodiments, a shell may be added on top and/or below the cushioning elements without compromising the cushioning function.

Because the cushioning layer comprises an array of discrete solid and resilient cushioning elements, the cushioning elements are able to react individually to an applied load, as opposed to cushioning structures arranged in cellular topologies. A cushioning structure in accordance with the present invention is therefore very versatile: cushioning can be applied over large and over small areas, and by changing the shape, the properties of the discrete cushioning elements, their dimensions, the number of elements per unit area, etc. the obtained deformation and the obtained supported pressure can vary in a very large range, and this can moreover be adapted, by the designer, from one area to another one. This is a way in which the present invention allows to provide a patient-specific prosthetic or orthotic device.

In embodiments, the prosthetic or orthotic device comprises a means for adjustment integrated into a main body of the prosthetic or orthotic device. Said means for adjustment may include screws, cylindrical or conical shapes which press against cushioning means directly or indirectly, e.g. press against a beam which itself presses against one or more cushioning means, which enables the application and/or adjustment of tension in one or more cushioning structures. In another embodiment, the means for adjusting properties of one or more cushioning means comprises of a cylinder with local elevations, protrusions and/or depressions. The cylinder presses against one or more cushioning elements, and by rotating the cylinder around its central axis, the tension in one or more cushioning structures can be adjusted. These adjustable structures can be built in to the same part as the cushioning means.

In any of the embodiments, rapid prototyping technology can be used to fabricate the orthotic/prosthetic device.

The devices or selected parts of the devices may also be impregnated or infiltrated with other substances such as resins, polymers, gels, elastomers to alter their properties such as color, hardness, flexural modulus, elongation at break, crack propagation, density and surface porosity.

The present invention also provides a method for designing an orthotic or prosthetic cushioned device, e.g. a computer based method, comprising the steps of:
  providing scan data describing at least part of the patient body;
  converting said scan data into a 3D virtual model on the basis of which a 3D design model of the orthotic or prosthetic device may be constructed;
  adding automatically or interactively at least one cushioning element from an electronic library of cushioning elements to said 3D design model and;
  fabricating the orthotic or prosthetic device.

Adding automatically or interactively at least one cushioning element from a library of cushioning elements to said 3D design model can include outputting a descriptor file of the orthotic or prosthetic device for fabrication purposes.

The present invention also provides a method for adjusting, modifying or arranging the cushioning elements manually with the means of adjustment or controlled fully automatically by the computer.

The present invention also provides a computer program comprising instructions that when executed on a computing device implement a method for:
  receiving scan data describing at least part of the patient body;
  converting said scan data into a 3D virtual model on the basis of which a 3D design model of the orthotic or prosthetic device may be constructed; and
  adding automatically or interactively at least one cushioning element from a library of cushioning elements to said 3D design model.

The computer program also comprises instructions for arranging the cushioning and adjustment structures manually or controlled fully automatically by the computer.

The computer program product can further comprise instructions for exporting a description file for fabricating an orthotic/prosthetic device from said design model of the orthotic/prosthetic device.

The present invention also includes a machine readable signal recording device on which is stored the computer program. Examples of computer readable signal bearing media include: recordable type media such as magnetic disks, e.g. floppy disks or hard disks; or optical disks such as CD ROMs, DD-ROMs; or solid state memory such as Random Access Memory, USB memory sticks, flash memory; or magnetic tape storage media; or transmission type media such as digital and analogue communication links.

BRIEF DESCRIPTION OF THE DRAWINGS

Embodiments of the invention will be described, by way of example only, with reference to the accompanying drawings in which:

FIG. 2 further illustrates a 2D representation of a beam.

DESCRIPTION OF PREFERRED EMBODIMENTS

Figure 1:
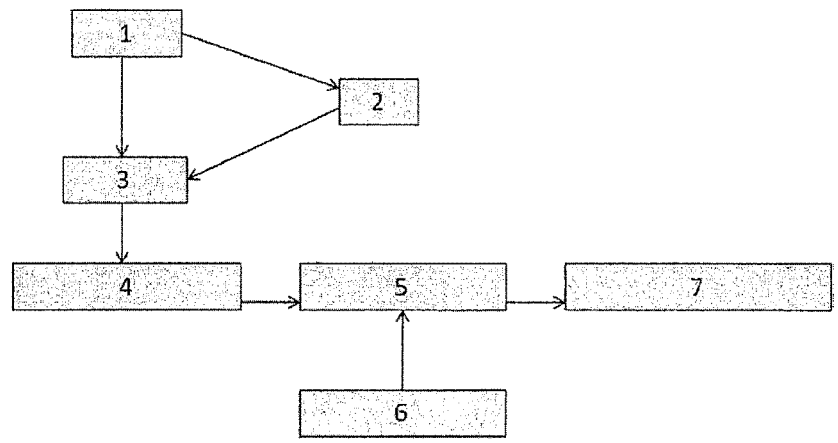
FIG. 1 shows a block diagram for designing and manufacturing an orthotic or prosthetic device comprising at least one cushioning layer.

In the following detailed description of the preferred embodiments, reference is made to the accompanying drawings, which form a part hereof, and within which are shown by way of illustration specific embodiments by which the invention may be practiced. The drawings described are only schematic and are non-limiting. In the drawings, the size of some of the elements may be exaggerated and not drawn on scale for illustrative purposes. Those skilled in the art will recognize that other embodiments may be utilized and structural changes may be made without departing from the scope of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In the following and in the attached claims reference may be made to a "patient". It should be understood that this term patient should be construed broadly to include not only humans but also animals in need of surgery.

In the following and in the attached claims reference may be made to an orthosis. It should be understood that an orthosis is an external insert, device, support or brace designed to support a patient in carrying the loads applied onto them by walking, running, manipulating objects and/or similar activities and/or by repositioning a limb or forcing them to move a certain way. They can also spread the pressure between the body and the shoe/ground/prosthetic over a larger surface area and provide cushioning to the loaded areas.

In the following and in the attached claims reference may be made to a prosthetic device or prosthesis. It should be understood that a prosthetic device is an artificial extension of, or addition to the human body or a replacement of a lost body part, e.g. to replace a lost limb or any other body part. A prosthetic limb—upper or lower extremity—usually consists of a prosthetic socket which conforms to the residual limb, the artificial limb itself, such as a hand or leg and some means of attaching the limb to the socket.

For means of explaining the invention in more detail, the following description refers to an ankle foot orthosis (AFO) that is usually a plastic brace attaching to the calf of the subject with a Velcro strap or lacing and with a sole part, fitting under the foot which in some cases can fit inside a shoe. The present invention is not limited to just such orthotic elements.

The purpose of an AFO is to control the ankle joint rotations and possibly carry some of the forces applied through the foot and ankle. Foot orthoses (FO) in the form of specially shaped inserts which fit inside the shoe, have been found to be effective for relieving pain and increasing mobility. It is believed that they work by removing pressure from painful areas and by re-aligning the foot. This is done by any of controlling abnormal or excessive subtalar-, and/or midtarsal joint motion, distributing the weight over a larger area and by offering cushioning and shock absorption, where it is needed. It should be understood however that the subject matter of this invention is also applicable to any other orthotic or prosthetic device, including, but not limited to, knee orthoses, knee-ankle-foot orthoses, hip orthoses, hip-knee-ankle-foot-orthosis, lumbar orthoses, transtibial-, transfemoral-, transradial-, transhumeral prosthesis—and prosthesis sockets, sockets/adaptors for bone anchored prosthetics and cranial helmets.

Referring now to the drawings, in particular FIG. 1, there is shown a block diagram that illustrates a preferred embodiment for designing and fabricating an orthotic or prosthetic device according to the present invention. First, the patient, illustrated by numeral 1 in FIG. 1, is sent to a scan facility with equipment for capturing a 3D image of the target surface, e.g. the limb. The scanning equipment in module 3 preferably generates a digitized data file that provides data describing the target surface, although the present invention is not limited to this form of record of the patient's anatomy. Next, in module 4 the scanned data may be imported into a computer program to convert the scanned data into a 3D virtual model of the patient's limb/residual limb. Alternatively, a cast of the limb/residual limb may be taken, as in module 2, which can then be scanned in module 3 by the scanning equipment. Once a virtual 3D model of the limb is constructed and is available in the computer, a 3D model of the orthoses/prosthesis may be designed based on the 3D model of the limb, as indicated by module 5. This design of the 3D model of the orthoses/prosthesis may be produced interactively or fully computer-controlled. As module 6 indicates, a library system of cushioning structures may be used in the design in order to incorporate a cushioning structure in the 3D computer model of the orthoses/prosthesis. Once the design is complete, it can be manufactured with a Rapid Prototyping process, as in module 7.

The limb or residual limb has always a certain shape, which is to be captured accurately in order to create a well-fitting orthoses/prosthesis. The geometry can be captured non-weight bearing or weight bearing through glass or Perspex (PMMA) or such transparent materials, which are pressed against the limb/residual limb. Alternatively, the patient can stand on the transparent plate and the weight bearing 3D shape obtained through the plate. The geometry of the limb/residual limb can be captured using the following means but not excluding other means of capturing it. In module 1 in FIG. 1, laser scanning technology may be used to generate a digital 3D geometry of the limb/residual limb shape. This can be in the form of a point cloud, a solid surface consisting of triangles or any other format for recording and storing a 3D geometry. Another way of obtaining the geometry is to manually make a plaster cast of the limb/residual limb and to use the technique described above to capture the shape of the cast. Alternatively, a positive made from the cast can be scanned. Making casts is how the "traditional" process works and to be able to accommodate this way of working is beneficial and the benefit is obvious to anyone skilled in the art. Apart from laser scanning, capturing the 3D geometry of the limb/residual limb may be done by means of radiation, e.g. X-rays or ultrasound or through computer tomography (CT) scans or magnetic resonance imaging (MRI) or any other scanning method known to generate medical volumetric data.

The geometry of the limb/residual limb determined in module 1 can be digitally imported into a computer program and may be converted using algorithms known from the field of CAD/CAM technology to produce a 3D computer model of the limb/residual limb. A computer program such as 3-Matic™ as supplied by Materialise N.V., Leuven, Belgium, may be used for constructing this 3D model. This geometry data can be used immediately in the computer program or stored in a digital file.

Once the 3D model of the limb/residual limb is constructed, it may be manipulated manually, semi-automatically or automatically to design a 3D model of the orthotic/prosthetic device. These manipulations may include one or more of the following processes but are not limited to:
1. Scaling the geometry smaller or larger along certain axis.
2. Giving the geometry a thickness that can be varied throughout the part.
3. In creating hollow volumes inside this thickness.
4. Adding new surface shapes in certain parts, such as local elevations.
5. Adding predetermined 3D elements from a database system (E).
6. Integrating the interventions made into an optimal orthotic/prosthetic shape.
7. Adding attachment features that enable the attachment of straps or other means to fasten the orthotic/prosthetic device to the person using it.
8. Adding holes or other features for ventilation purposes.

A preferred method for performing these actions uses a computer program such a 3-matic as supplied by Materialise N. V., Leuven, Belgium.

A data base library 6 of one or more 3D models of cushioning structures comprising cushioning elements or their mathematical representations may then be used to incorporate at least one cushioning element into the 3D model of the orthotic/prosthetic device. The elements in the library may be selected manually or automatically from the database by their pre-determined properties, such as their physical dimensions, their appearance or their mechanical properties, e.g. the spring coefficient, crack formation and crack propagation. It is to be understood that the dimensions and values regarding the performance of all cushioning elements available in the library may be scaled in any dimension to obtain the preferred or expected mechanical properties and performance. Functions representing them and their performance are preferably stored in this data base so that they can be called up when required, automatically or manually by the user, and integrated into the 3D design of the orthoses/prosthesis using the design software. Specific elements may be called from the library or all elements matching certain performance parameters for the user to select for a particular location and purpose may be called. More than one element can be selected by the library system to give certain areas of cushioning structures specific properties.

Figure 2:
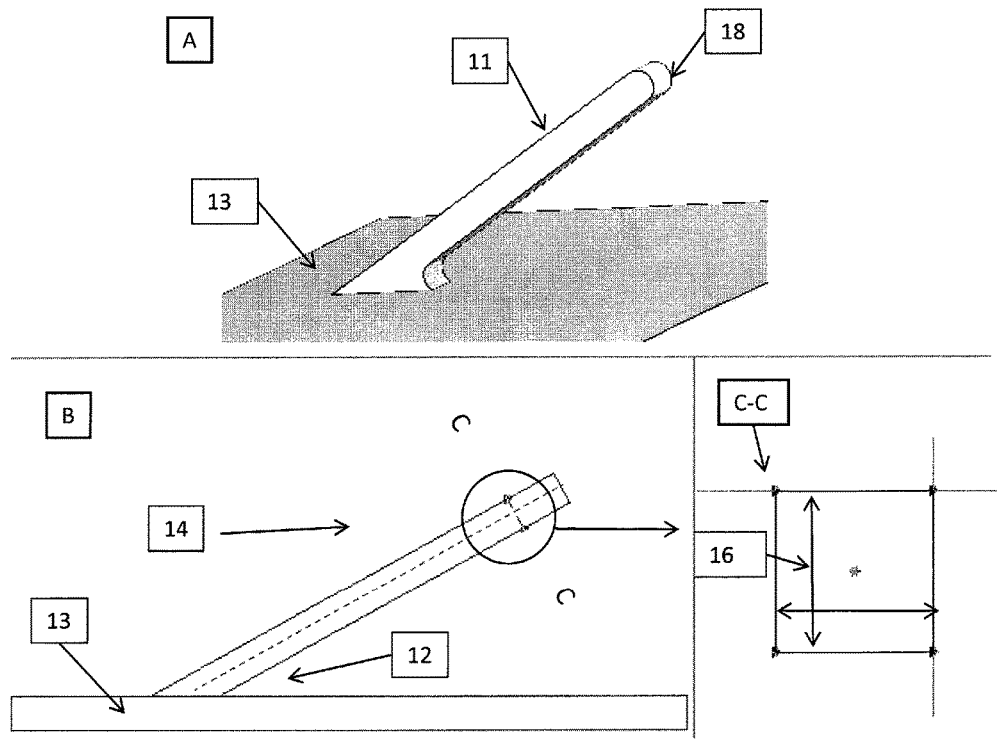
FIG. 2 illustrates cushioning elements according to an embodiment of the present invention.

In one preferred embodiment, according to FIG. 2, the cushioning structure consists of one or more absorbing means such as a bending moment absorbing means or a compression absorbing means. The absorbing means may be formed from one or more beams. The beams may be cantilevered from one end thereof, or may be anchored at both ends thereof. An absorbing means such as a beam is defined as any structure which shape can be clearly defined and capable of absorbing the contact forces placed on the absorbing means, e.g. beam by elastically deforming, e.g. by bending and/or by compression. The deformation of one or more absorbing means such as beams may create a sensation of having a soft surface if in contact with the skin.

The cushioning properties of a structure refer to it being compressibly resilient. This can mean the compressibility of the material, the elastic deformation of the structure or a combination thereof. This can be measured for example with the standard ISO 7619 or ASTM D2240. The areas of the orthotic/prosthetic device that are cushioned using the embodiments described in this invention have the Shore value of 20-90 when measured using an OO durometer using these standards. This cushioning structure is not foam. Each shape and feature in the cushioning structure is determined deliberately either by the user or the computer system. Shapes and features in the cushioning structure can be seamlessly adjusted as needed by the computer system or the user.

Figure 3:
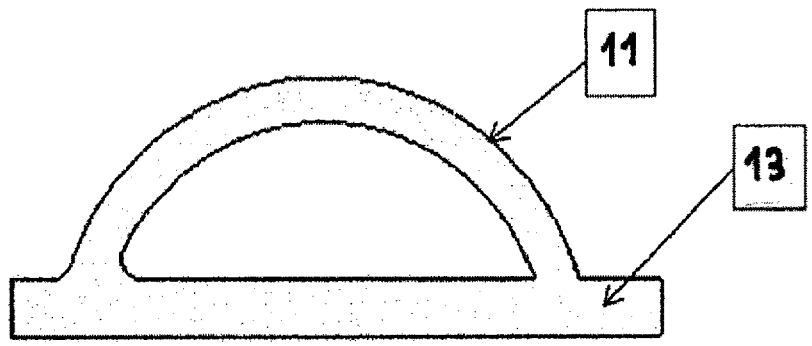
FIG. 3 illustrates a cushioning element according to an embodiment of the present invention.
Figure 4:
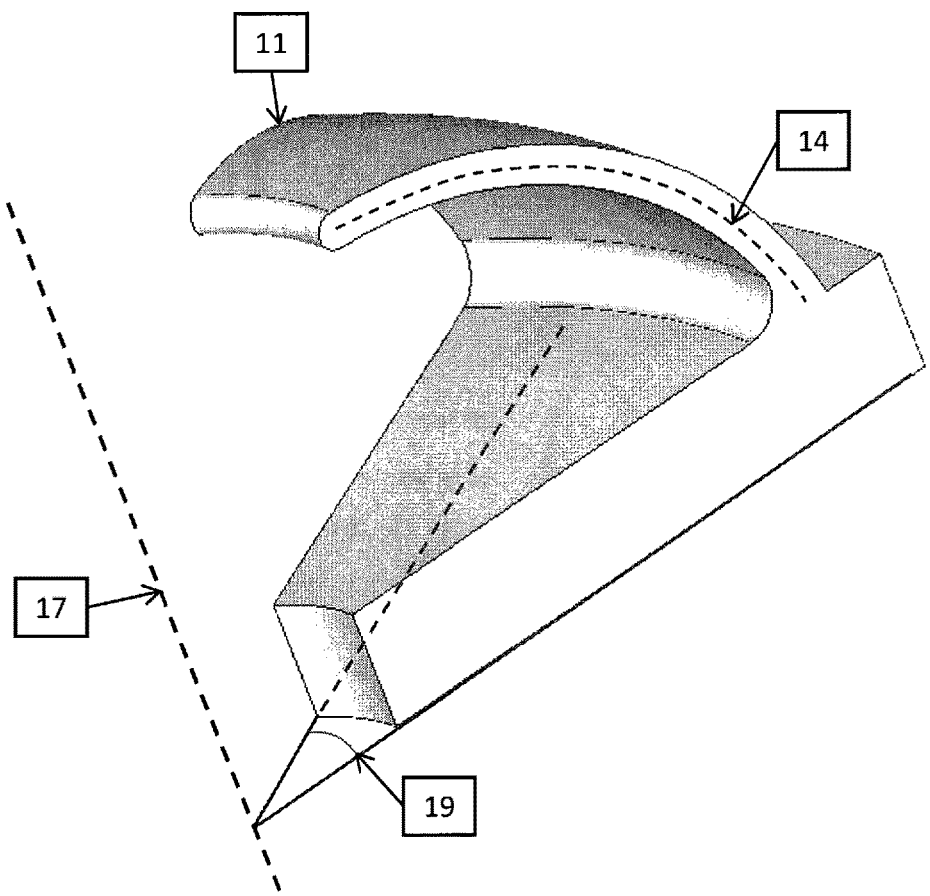
FIG. 4 illustrates a 3D representation of a profile rotated around an axis according to an embodiment of the present invention.

In FIG. 2, beam 11 protrudes from main body 13 with an angle 12 that may vary for other cushioning elements. The beam centreline 14 is preferably linear or curved but may have any arbitrary shape. Preferably, the beam cross-section 16 has a rectangular shape, but may have any other arbitrary shape including but not limited to a circular, triangular, semi-circular, elliptical, or square shape. The cross-section may also vary within beam 11 along centreline 14 as needed. This will result in a great number of different beam shapes, which can be designed as necessary. Beam 11 can also have a radius where it attaches to main body 13 of the orthoses/prosthesis to decrease local tensions. The end of the protrusion may also be rounded to improve comfort if the protrusion is in contact directly with the user as indicated by numeral 18 in FIG. 2A. In another embodiment, the portion of cushioning elements that may be in direct contact with the user may be made from another, suitable material. As illustrated in FIG. 3, beam 11 may also re-connect with the main body 13 where it started from. In FIG. 4, the centreline 14 of the beam 11 has been rotated around an axis 17 over an angle 19. This can be done to any profile described previously to create yet more different cushioning elements.

Figure 5:
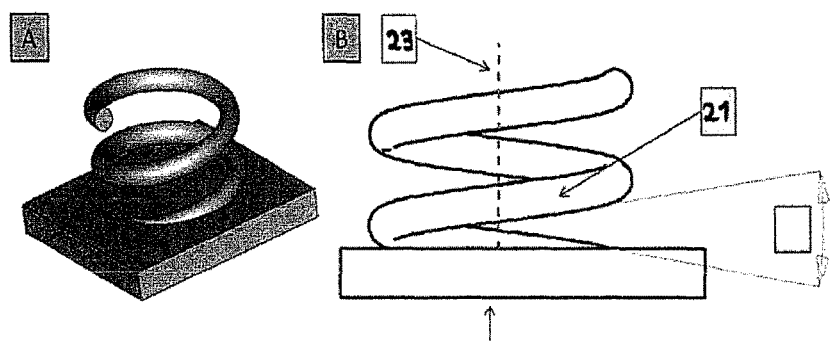
FIG. 5 illustrates 2D representations of a spiral spring structure according to an embodiment of the present invention.

In another preferred embodiment, according to FIG. 5, the cushioning element is a beam in the shape of a spiral 21. Preferably, a cylindrical spiral 21 with a circular cross-section is used, however, the spiral may revolve around any other geometry, including but not limited to a cone or an elliptical cylinder and may have any arbitrary shape as a cross-section. Preferably, the axis 23 around which the spiral revolves is straight, but it may have any arbitrary shape or follow any curve defined by a mathematical function. In addition, another spring may also be placed inside spiral 21—space permitting.

It should be understood that any combination of the previous embodiments as described above is also within the scope of the invention.

Figure 6:
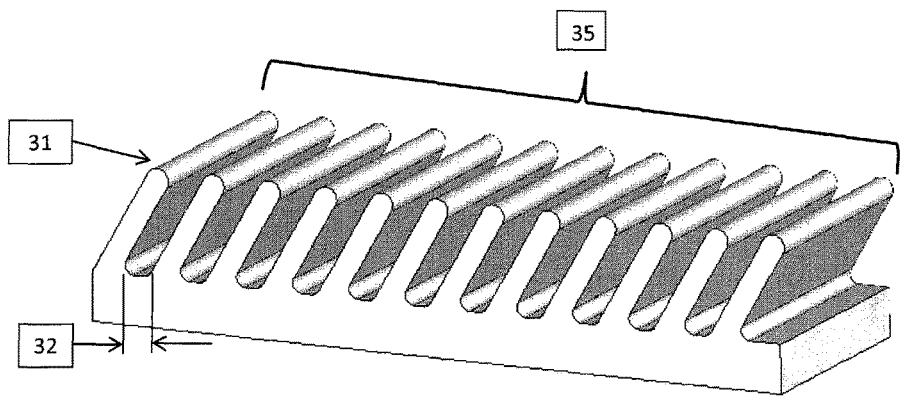
FIG. 6 illustrates an array of cushioning elements according to an embodiment of the present invention.
Figure 7:
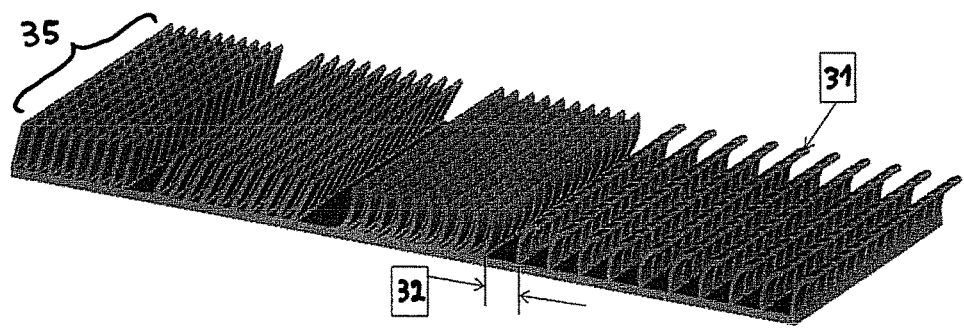
FIG. 7 illustrates an array of cushioning elements according to an embodiment of the present invention.
Figure 8:
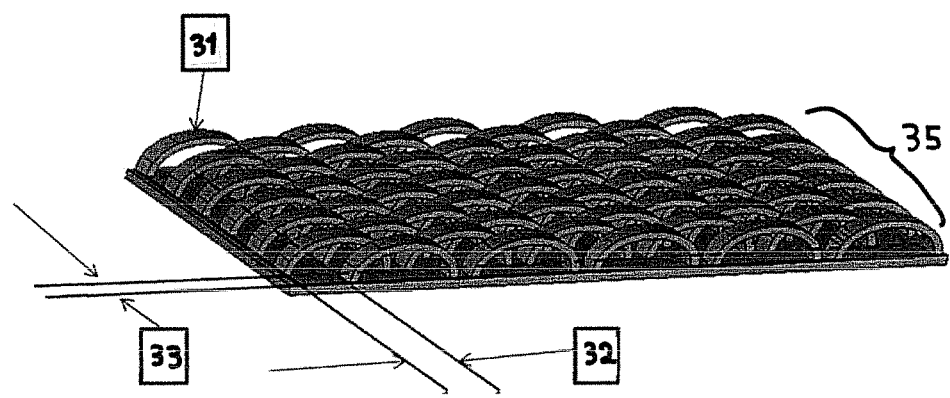
FIG. 8 illustrates an array of the cushioning elements according to an embodiment of the present invention.

The cushioning elements may be patterned to create areas of cushioning. The cushioning areas can consist of identical cushioning elements or have several different element types mixed up. In FIG. 6, a simple pattern is displayed where several cushioning elements 31 are placed along a line with spacing 32. In FIG. 7, several more patterns are illustrated, where the patterns have also been separated by a spacing or gap 32. FIGS. 6 and 7 illustrate a cushioning layer comprising an array 35 of discrete cushioning elements 31. As illustrated in FIG. 8, cushioning elements 31 may also be placed next to each other with a separation distance 32 and 33 in two directions. Apart from having spacing between each other, the cushioning elements may also be placed at an angle in relation to each other. The cushioning areas may be defined e.g. on the basis of a pressure map or using markers with a useful meaning that have been added to the 3D model of the limb and may include large weight-bearing areas, such as plantar surfaces on the foot or under a residual limb in a prosthetic socket, smaller weight-bearing areas or areas of elevated contact pressure with the ground and/or the orthotic/prosthetic device, such as calluses, joints or local deformities, parts of the orthotic/prosthetic that are in contact with the skin or any other areas of interest designated by a person skilled in the art. The cushioning areas may be created manually by selecting various cushioning elements from the library or may be automatically generated. For the latter, measurement data may be imported to the design software, which then uses this data to select suitable structures according to logic programmed therein and to place those structures automatically where needed. For example, a pressure distribution measurement can be imported into the system and if certain locations/areas have pressure values matching a predetermined range of values, the library system places specific features on those locations/areas automatically. The designer can then accept or modify the proposed design in any arbitrary way.

The thickness of the cushioning elements 11, 21, 31, such as illustrated in FIGS. 2-13, is typically between 0.5 and 3 mm, depending on the application. For applications involving high loads, larger thicknesses may be used. In a preferred embodiment, the thickness is less than 5 mm. The maximum dimension (length, width or height) of a bounding box having the form of a rectangular parallellepid just surrounding a cushioning element is preferably less than 2 cm, more preferably less than 1 cm.

Figure 9:
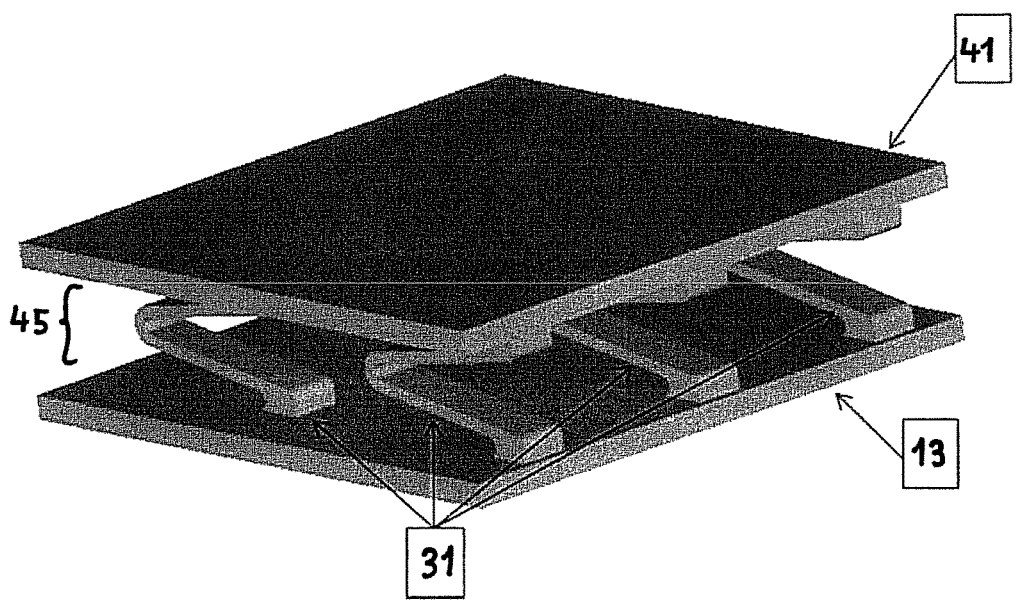
FIGS. 9 to 13 show illustrations of cushioning structures according to embodiments of the present invention.

Having placed, as indicated in FIG. 9, a cushioning layer 45 of cushioning elements 31 on the orthotic or prosthetic shell 13 of the orthotic/prosthetic devices, an additional shell 41, may be created on top of the cushioning elements 31 attached to the orthotic or prosthetic shell 13. This additional shell 41 can also be created on top of a locally indicated area creating a hollow volume with cushioning elements inside. If the shell is thin and/or rigid enough, this will allow the surface to deform further absorbing forces placed on it and it also allows the cushioning elements below it to also deform and absorb forces. If the shell is sufficiently rigid, it will spread the load placed on it to the structures below if several structures are present. The stiffer the shell is, the larger the area that will carry the loads. The thickness of the shell may be varied throughout the surface to alter its properties and the way it spreads the load with the structures underneath. The shell may also act as a further cushioning means depending on the compression ability of the structure. Another layer of cushioning elements may be added on top of this and there can be as many of these "sandwiched" layers as needed. The resistance to deformation of the surface and the cushioning elements may be controlled by altering the cushioning elements' shape, geometry, material property, the manufacturing or post-processing process parameters or any combination thereof creating a controllable cushioning effect.

Moreover, the sandwiched cushioning layers may have different properties (e.g. by using different cushioning elements, different materials for the cushioning elements, etc.). An advantage of these sandwiched layers is to make use of each of these properties.

Further, one or more of the sandwiched cushioning layers may comprise different areas that have mutually different cushioning properties, obtained e.g. by the use of cushioning elements having different shapes, materials, dimensions, by using a different number of elements per unit area, etc.

The cushioning structures may comprise a means for adjusting. Said means for adjustment may include a movable surface, beam or a "plateau" that modifies at least one meaningful property of the cushioning structure such as the spring coefficient, range of movement, and the like. These features accomplish a modification of at least one meaningful property by pressing against the cushioning structure and preventing motion or creating tension in the structure. This changes the deformability and compressibility of the structure. The moveable surface can also be inserted between the deforming section of the cushioning structure and the main body of the orthoses or prosthesis modifying the properties of the deforming structure.

Figure 10:
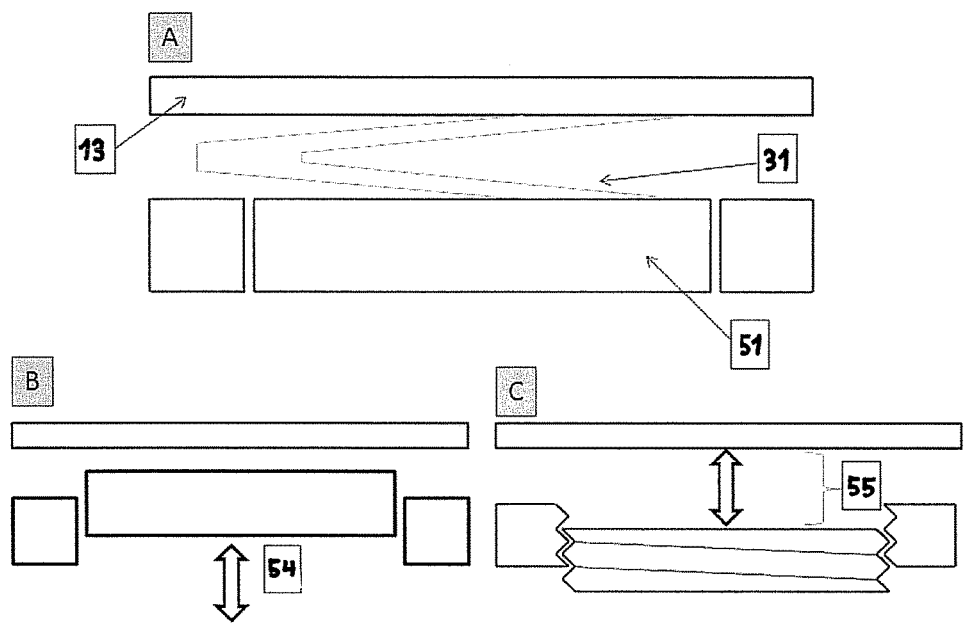
Figure 11:
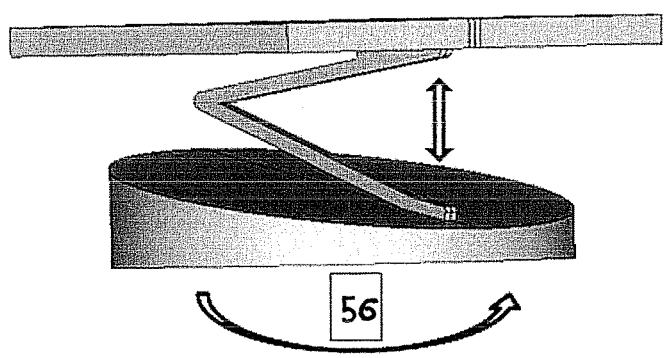

In one preferred embodiment, the means for adjustment may be a cylindrical surface as indicated by 51 in module A in FIG. 10 that presses the cushioning element 31 towards the orthotic or prosthetic shell 13. This surface 51 can be moved towards the cushioning elements through means of linear motion as indicated by 54 in module B in FIG. 10 between the main orthoses/prosthesis body, restricting the movement of the cushioning elements and thus adjusting the cushioning effect. In one embodiment, this linear motion is accomplished rotating a threaded cylinder as indicated by 55 in module C in FIG. 10 such as e.g. a screw. Furthermore, the top surface of the cylinder may be flat or be inclined as indicated by 56 in FIG. 11 or undulating or any combination thereof, offering more possibilities with adjustment.

Figure 12:
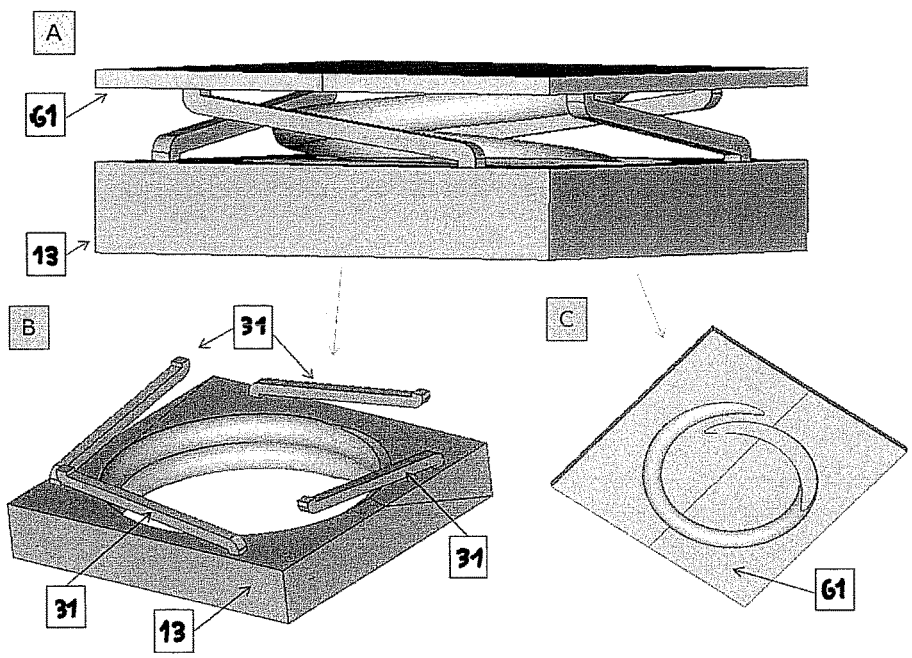

The surface on top of the cushioning structure as indicated by 61 in module A and B in FIG. 12 can also move, if not attached to the main orthoses/prosthesis body 13 in module A and C. In one preferred embodiment, upper surface 61 in module A and B is connected through the means of non-adjustable cushioning elements 31 in module B.

In another embodiment, an actuator or any other device is used to move the moveable surface or one or more beams connected to one or more cushioning structure allowing for the adjustment of several structures simultaneously.

Figure 13:
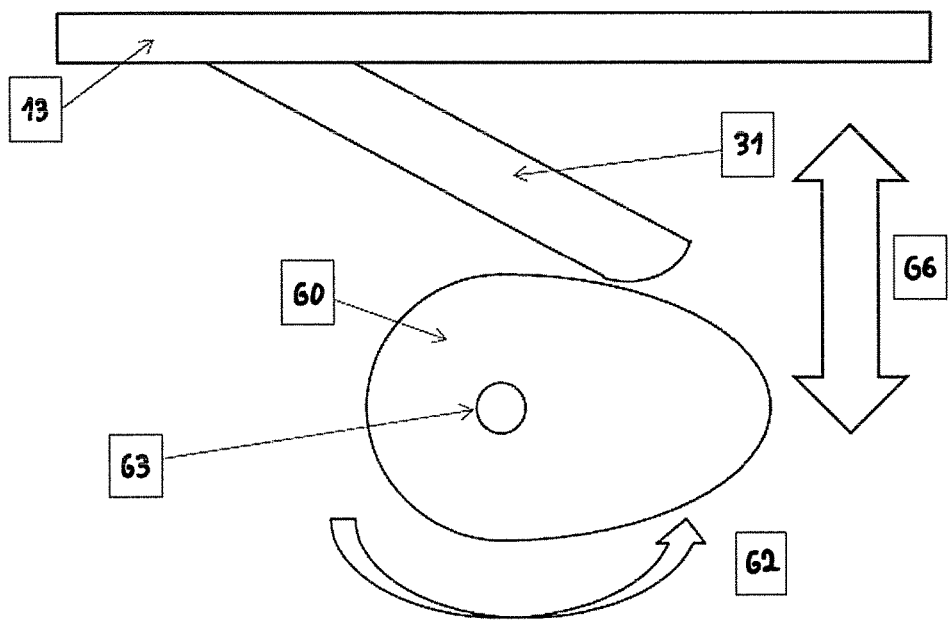

Another means of adjusting a cushioning element is presented in FIG. 13, where a round, elliptical, concentric or cylinder or one consisting of any combination thereof (60), can be rotated (62) around an axis (63) perpendicular to the normal of the inner surface of the orthotic/prosthetic (13). The rotation causes the cushioning element (31) in contact with the cylinder to become loaded or unloaded (66), adjusting its properties.

Figure 14:
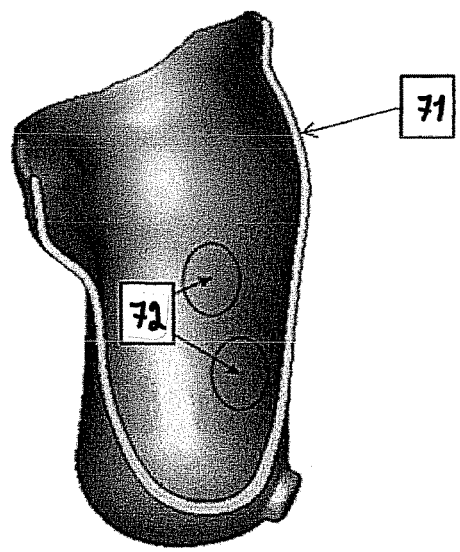
FIG. 14 shows a 3D representation of a prosthesis socket indicating possible locations for the cushioning structures.
Figure 15:
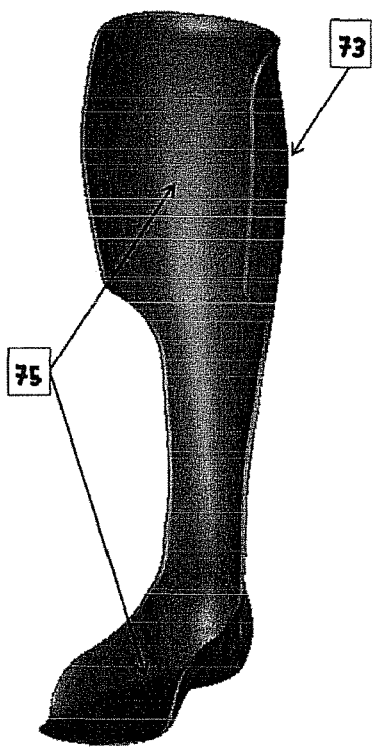
FIG. 15 shows a 3D representation of an orthotic device indicating possible locations for cushioning structures.

FIG. 14 schematically shows a transtibial prosthetic socket 71 that contains cushioning structures in cushioning areas 72 that cushion the weight bearing parts of the prosthesis 71 and surface areas 72 in contact with the most sensitive areas as known by a person skilled in the art. FIG. 15 displays an orthosis 73, where similar surface cushioning or cushioning on weight bearing areas 75 is needed. The surface and weight bearing types can be combined in the same structure.

Figure 16:
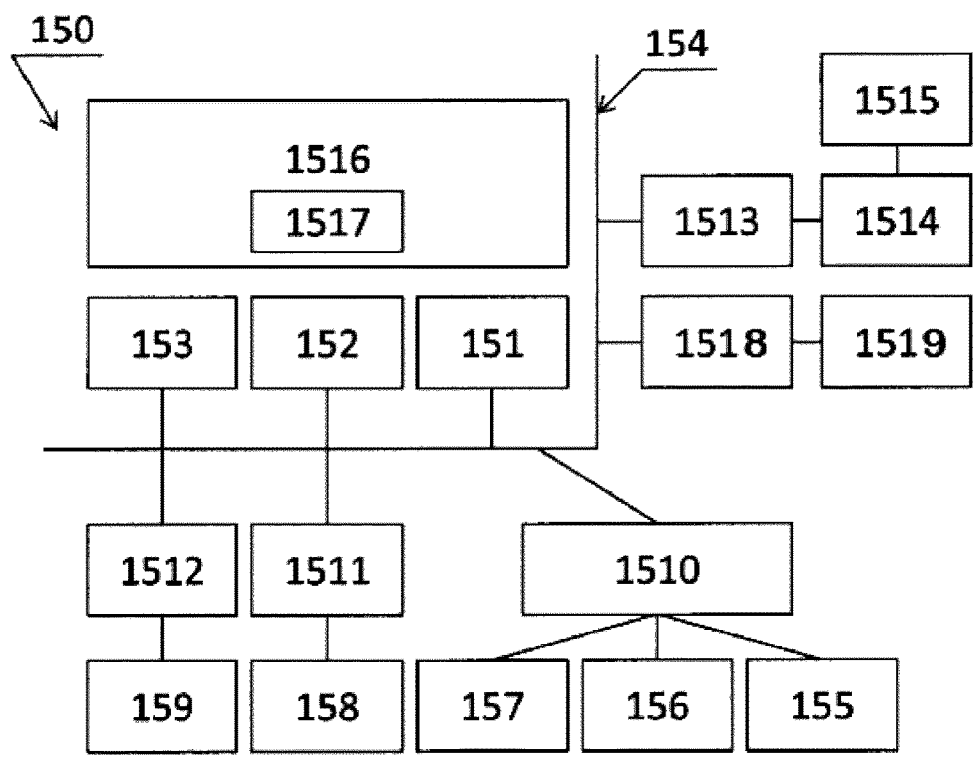
FIG. 16 illustrates a computer based system for use with embodiments of the present invention. The computer based system may include the following parts: a computer (150), a computer memory storage (1516), a control program (1517), ROM (153), RAM (152), CPU (151), a display adapter (1512), an input/output (I/O) adapter (1511), a user interface adapter (1510), a video display terminal (159), disk and tape drives (158), a speaker (157), a mouse (156), a keyboard (155), a communications adapter (1518), and/or a CAD/CAM manufacturing unit (1519). The computer may further include a computer adapter (1513) connected to a data network (1514) connected to a far location (1515).

FIG. 16 is a schematic representation of a computing system which can be utilized with the methods and in a system according to the present invention including computer programs such as 3-Matic™ as supplied by Materialise N. V., Leuven, Belgium. A computer 150 is depicted which may include a video display terminal 159, a data input means such as a keyboard 155, and a graphic user interface indicating means such as a mouse 156. Computer 150 may be implemented as a general purpose computer, e.g. a UNIX workstation or a personal computer.

Computer 150 includes a Central Processing Unit ("CPU") 151, such as a conventional microprocessor of which a Pentium processor supplied by Intel Corp. USA is only an example, and a number of other units interconnected via bus system 154. The bus system 154 may be any suitable bus system—FIG. 16 is only schematic. The computer 150 includes at least one memory. Memory may include any of a variety of data storage devices known to the skilled person such as random-access memory ("RAM"), read-only memory ("ROM"), non-volatile read/write memory such as a hard disc as known to the skilled person. For example, computer 150 may further include random-access memory ("RAM") 152, read-only memory ("ROM") 153, as well as a display adapter 1512 for connecting system bus 154 to a video display terminal 159, and an optional input/output (I/O) adapter 1511 for connecting peripheral devices (e.g., disk and tape drives 158) to system bus 154. Video display terminal 159 can be the visual output of computer 150, which can be any suitable display device such as a CRT-based video display well-known in the art of computer hardware. However, with a desk-top computer, a portable or a notebook-based computer, video display terminal 159 can be replaced with a LCD-based or a gas plasma-based flat-panel display. Computer 150 further includes user interface adapter 1510 for connecting a keyboard 155, mouse 156, optional speaker 157. The relevant data describing the 3-D object to be formed may be input directly into the computer using the keyboard 155 or from storage devices such as 158, after which a processor carries out a method in accordance with the present invention. The results of the method may be transmitted to a further near or remote location, e.g. a CAD/CAM processing facility to manufacture the template in accordance with the details provided by computer 150.

A CAD/CAM manufacturing unit 1519 may also be connected via a communications adapter 1518 to bus 154 connecting computer 150 to a data network such as the Internet, an Intranet a Local or Wide Area network (LAN or WAN) or a CAN. The manufacturing unit 1519 may receive an output value or support descriptor file directly from computer 150 running a computer program for support design in accordance with the present invention or a value or descriptor file derived from such an output of computer 150. Alternatively, the unit 1519 may receive the relevant design data indirectly on a suitable signal storage medium such as a diskette, a replaceable hard disc, an optical storage device such as a CD-ROM or DVD-ROM, a magnetic tape or similar.

Computer 150 also includes a graphical user interface that resides within machine-readable media to direct the operation of computer 150. Any suitable machine-readable media may retain the graphical user interface, such as a random access memory (RAM) 152, a read-only memory (ROM) 153, a magnetic diskette, magnetic tape, or optical disk (the last three being located in disk and tape drives 158). Any suitable operating system and associated graphical user interface (e.g., Microsoft Windows, Linux) may direct CPU 151. In addition, computer 150 includes a control program 1517 that resides within computer memory storage 1516. Control program 1517 contains instructions that when executed on CPU 151 allow the computer 150 to carry out the operations described with respect to any of the methods of the present invention.

Those skilled in the art will appreciate that the hardware represented in FIG. 16 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already described.

In the example depicted in FIG. 16, the computer program product for carrying out the method of the present invention can reside in any suitable memory. However, it is important that while the present invention has been, and will continue to be, that those skilled in the art will appreciate that the mechanisms of the present invention are capable of being distributed as a computer program product in a variety of forms, and that the present invention applies equally regardless of the particular type of signal bearing media used to actually carry out the distribution. Examples of computer readable signal bearing media include: recordable type media such as floppy disks and CD ROMs and transmission type media such as digital and analogue communication links.

Accordingly, the present invention also includes a software product which when executed on a suitable computing device carries out any of the methods of the present invention. Suitable software can be obtained by programming in a suitable high level language such as C and compiling on a suitable compiler for the target computer processor.

Having designed the orthotic or prosthetic device, it can be manufactured, as illustrated as module 6 in FIG. 1. In one preferred embodiment, Rapid Prototyping and Manufacturing (RP&M) techniques are used to manufacture the device. Rapid Prototyping and Manufacturing (RP&M) can be defined as a group of techniques used to quickly fabricate a scale model of an object typically using three-dimensional (3-D) computer aided design (CAD) data of the object. Currently, a multitude of Rapid Prototyping techniques is available, including stereo lithography (SLA), Selective Laser Sintering (SLS), Fused Deposition Modeling (FDM), foil-based techniques, etc.

A common feature of these techniques is that objects are typically built layer by layer. Stereo lithography, presently the most common RP&M technique, utilizes a vat of liquid photopolymer "resin" to build an object a layer at a time. On each layer, an electromagnetic ray, e.g. one or several laser beams which are computer-controlled, traces a specific pattern on the surface of the liquid resin that is defined by the two-dimensional cross-sections of the object to be formed. Exposure to the electromagnetic ray cures, or, solidifies the pattern traced on the resin and adheres it to the layer below. After a coat had been polymerized, the platform descends by a single layer thickness and a subsequent layer pattern is traced, adhering to the previous layer. A complete 3-D object is formed by this process.

Selective laser sintering (SLS) uses a high power laser or another focused heat source to sinter or weld small particles of plastic, metal, or ceramic powders into a mass representing the 3-dimensional object to be formed.

Fused deposition modeling (FDM) and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically RP&M techniques start from a digital representation of the 3-D object to be formed. Generally, the digital is sliced into a series of cross-sectional layers which can be overlaid to form the object as a whole. The RP&M apparatus uses this data for building the object on a layer-by-layer basis. The cross-sectional data representing the layer data of the 3-D object may be generated using a computer system and computer aided design and manufacturing (CAD/CAM) software.

A selective laser sintering (SLS) apparatus is particularly preferred for the manufacture of the orthotic or prosthetic device from a computer model. It should be understood however, that various types of rapid manufacturing and tooling may be used for accurately fabricating these orthotic or prosthetic devices including, but not limited to, stereolithography (SLA), Fused Deposition Modeling (FDM) or milling.

The orthotic or prosthetic device may be manufactured in different materials. Preferably, only materials that are biocompatible with the human body are taken into account. In the case SLS is used as a RP&M technique, the orthotic or prosthetic device may be fabricated from a polyamide such as PA 2200 as supplied by EOS, Munich, Germany or Duraform PA from 3D Systems, South Caroline, USA, or any other material known by those skilled in the art may also be used. The orthotic/prosthetic may also be painted and/or coated using any suitable means.

The present invention may provide one or more of the following advantages:

The quality of the devices is more consistent as significant manual intervention is no longer needed.

Less labour is needed. The labor does not need to be as skilled in all of the manual work phases. Only in scanning, CAD design, finishing and fitting the parts.

Less production equipment may be needed (one machine).

The current invention may result in less waste from the manufacturing process.

The current invention may result in a faster production.

The current invention may result in more automated production.

With the current invention, there is no longer a need to store casts as everything can be stored digitally and reproduced as needed. Also, the whole orthotic/prosthetic treatment history of the patient is available for clinicians to use when needed.

Built in adjustability gives the clinician more options when the orthoses or prosthetic is fitted on the patient. Also, if there is a change in the patient's condition, and/or shape of the limb/residual limb, the adjustable device can still provide a good fit and functionality.

What is claimed is:

1. An orthotic or prosthetic device comprising:
a plurality of orthotic or prosthetic shells and a plurality of cushioning layers forming a sandwich structure,
the plurality of cushioning layers comprising an array of discrete solid, deformable, and compressibly resilient cushioning elements that are homogenously formed with the plurality of orthotic or prosthetic shells, wherein one or more of the cushioning elements of the array comprises a beam that is wider in a first direction than in a second direction and comprises a first side and a second side opposite the first side, wherein the first side is superimposed onto a first shell of the plurality of orthotic or prosthetic shells and wherein the second side is superimposed onto a second shell of the plurality of orthotic or prosthetic shells that is different from the first shell.

2. The orthotic or prosthetic device of claim 1, wherein the array of cushioning elements and said plurality of orthotic or prosthetic shells are formed from the same material.

3. The orthotic or prosthetic device of claim 1, wherein said plurality of cushioning layers comprise a plurality of different types of cushioning elements.

4. The orthotic or prosthetic device of claim 1, wherein at least one of the plurality of cushioning layers comprises a first cushioning area having first cushioning properties and a second cushioning area having second cushioning properties different from the first cushioning properties for adapting the orthotic or prosthetic device to a patient.

5. The orthotic or prosthetic device of claim 1, wherein the first side and the second side of the beam each comprise one of an end of the beam, an edge of the beam, or a surface of the beam.

6. The orthotic or prosthetic device of claim 1, wherein the beam protrudes from at least one of the first shell or the second shell at an angle.

7. The orthotic or prosthetic device of claim 6, wherein the angle is less than 90°.

8. The orthotic or prosthetic device of claim 1, wherein the beam comprises a centerline that is rotated around an axis over an angle.

9. The orthotic or prosthetic device of claim 1, wherein the beam comprises folds configured to deform when absorbing forces.

10. The orthotic or prosthetic device of claim 1, wherein the beam revolves around a geometry comprising at least one of a spiral, a cone, an elliptical cylinder, or an angle.

11. The orthotic or prosthetic device of claim 10, wherein the geometry around which the beam revolves is at least one of straight, curved, or following an arbitrary shape.

12. The orthotic or prosthetic device of claim 10, wherein a second beam is placed inside a boundary formed by the beam that revolves around the geometry.

13. The orthotic or prosthetic device of claim 1, wherein at least a portion of the beam has a rectangular cross section.

14. The orthotic or prosthetic device of claim 1, wherein the sandwich structure forms a hollow volume with the array of cushioning elements inside.

15. The orthotic or prosthetic device of claim 1, wherein the cushioning elements in the array are spaced apart along a line.

16. The orthotic or prosthetic device of claim 1, wherein the cushioning elements in the array are placed next to each other with a separation distance in two directions.

17. The orthotic or prosthetic device of claim 1, wherein the cushioning elements in the array are placed at an angle in relation to each other.

18. The orthotic or prosthetic device of claim 1, further comprising at least one second beam having a first side that is superimposed onto at least one of the first shell, the second shell, or a third shell of the plurality of orthotic or prosthetic shells and a second side for contacting a part of at least one of a user or an item directly contacting the user.

19. The orthotic or prosthetic device of claim 1, wherein each of the cushioning elements is located on the plurality of cushioning layers based on a user-specific design.

20. A device configured to be worn by a user, comprising:
a body arranged to spread pressure between a body part of the user and the device; and
a plurality of orthotic or prosthetic shells and a plurality of cushioning layers forming a sandwich structure, the plurality of cushioning layers comprising an array of discrete solid, deformable, and compressibly resilient cushioning elements homogenously formed with the body, wherein one or more of said cushioning elements of the array comprises a beam that is wider in a first direction than in a second direction and comprises a first side and a second side opposite the first side, wherein the first side is superimposed onto a first shell of the plurality of orthotic or prosthetic shells and wherein the second side is superimposed onto a second shell of the plurality of orthotic or prosthetic shells that is different from the first shell.

* * * * *